(12) United States Patent
Matthews et al.

(10) Patent No.: US 7,245,956 B2
(45) Date of Patent: Jul. 17, 2007

(54) UNOBTRUSIVE MEASUREMENT SYSTEM FOR BIOELECTRIC SIGNALS

(75) Inventors: Robert Matthews, San Diego, CA (US); Igor Fridman, San Diego, CA (US); Paul Hervieux, San Diego, CA (US)

(73) Assignee: Quantum Applied Science & Research, Inc., San Diego, CA (US)

( * ) Notice: Subject to any disclaimer, the term of this patent is extended or adjusted under 35 U.S.C. 154(b) by 195 days.

(21) Appl. No.: 10/919,461

(22) Filed: Aug. 17, 2004

(65) Prior Publication Data

US 2006/0015027 A1    Jan. 19, 2006

Related U.S. Application Data

(60) Provisional application No. 60/588,045, filed on Jul. 15, 2004.

(51) Int. Cl.
*A61B 5/0408* (2006.01)
(52) U.S. Cl. .................... 600/382; 600/386; 600/393
(58) Field of Classification Search ................ 600/382, 600/386, 393
See application file for complete search history.

(56) References Cited

U.S. PATENT DOCUMENTS

| | | | |
|---|---|---|---|
| 3,043,291 A | 7/1962 | Nielson | |
| 3,409,007 A | 11/1968 | Fuller | |
| 3,476,104 A | 11/1969 | Davis | |
| 3,500,823 A | 3/1970 | Richardson et al. | |
| 3,565,060 A | 2/1971 | Sipple | |
| 3,620,208 A | 11/1971 | Higley et al. | |
| 3,722,677 A | 3/1973 | Lehnert | |
| 3,744,482 A | 7/1973 | Kaufman et al. | |
| 3,880,146 A | 4/1975 | Everett et al. | |
| 3,882,846 A | 5/1975 | Fletcher et al. | |
| 3,888,240 A * | 6/1975 | Reinhold et al. | ........... 600/390 |
| 3,923,042 A | 12/1975 | Hajdu et al. | |
| 3,954,100 A * | 5/1976 | Sem-Jacobsen | ............. 600/393 |
| 4,248,244 A | 2/1981 | Charnitski et al. | |
| 4,580,576 A | 4/1986 | Blackwood | |

(Continued)

FOREIGN PATENT DOCUMENTS

CA    2280996    2/2001

(Continued)

OTHER PUBLICATIONS

Author Unknown, "Ultra Low Input Bias Current Instrumentation Amplifier," Burr-Brown Corp., pp. 1-9, 1994.

(Continued)

*Primary Examiner*—Lee S. Cohen
(74) *Attorney, Agent, or Firm*—Diederiks & Whitelaw PLC

(57) ABSTRACT

A system for unobtrusively measuring bioelectric signals developed by an individual includes multiple sensors, one or more of which constitutes a capacitive sensor, embedded into or otherwise integrated into an object, such as a chair, bed or the like, used to support the individual. The object serves as mounting structure that holds the sensors in place. The sensors are preferably arranged in the form of an array, with particular ones of the sensors being selectable from the array for measuring the bioelectric signals which are transmitted, such as through a wireless link, for display and/or analysis purposes.

20 Claims, 5 Drawing Sheets

U.S. PATENT DOCUMENTS

| | | | |
|---|---|---|---|
| 4,581,821 A | 4/1986 | Cahalan et al. | |
| 4,602,639 A | 7/1986 | Hoogendoorn et al. | |
| 4,669,479 A | 6/1987 | Dunseath, Jr. | |
| 4,688,141 A | 8/1987 | Bernard et al. | |
| 4,698,848 A | 10/1987 | Buckley | |
| 4,709,704 A | 12/1987 | Lukasiewicz | |
| 4,785,237 A | 11/1988 | Cox | |
| 4,801,866 A | 1/1989 | Wixley | |
| 4,889,123 A | 12/1989 | Lee | |
| 5,001,594 A | 3/1991 | Bobbio | |
| 5,015,906 A | 5/1991 | Cho et al. | |
| 5,039,312 A | 8/1991 | Hollis, Jr. et al. | |
| 5,090,643 A | 2/1992 | Spears | |
| 5,119,404 A | 6/1992 | Aihara | |
| 5,169,380 A | 12/1992 | Brennan | |
| 5,191,891 A | 3/1993 | Righter | |
| 5,229,593 A | 7/1993 | Cato | |
| 5,257,631 A * | 11/1993 | Wilk | 600/508 |
| 5,289,822 A | 3/1994 | Highe et al. | |
| 5,304,941 A | 4/1994 | Tateishi | |
| 5,313,942 A | 5/1994 | Platzker | |
| 5,325,073 A | 6/1994 | Hasegawa | |
| 5,336,999 A | 8/1994 | Mansfield et al. | |
| 5,348,008 A | 9/1994 | Bornn et al. | |
| 5,485,092 A | 1/1996 | Fortin | |
| 5,488,677 A | 1/1996 | Tokano | |
| 5,574,805 A | 11/1996 | Toba et al. | |
| 5,632,280 A | 5/1997 | Leyde et al. | |
| 5,645,527 A | 7/1997 | Beck | |
| 5,650,750 A | 7/1997 | Leyde et al. | |
| 5,670,870 A | 9/1997 | Muramatsu | |
| 5,699,015 A | 12/1997 | Dotson et al. | |
| 5,734,296 A | 3/1998 | Dotson et al. | |
| 5,751,192 A | 5/1998 | Main | |
| 5,781,003 A | 7/1998 | Kondo | |
| 5,795,293 A | 8/1998 | Carim et al. | |
| 5,798,673 A | 8/1998 | Griffith et al. | |
| 5,803,911 A | 9/1998 | Inukai et al. | |
| 5,896,035 A | 4/1999 | Takahashi | |
| 5,947,920 A | 9/1999 | Beck | |
| 5,993,401 A | 11/1999 | Inbe et al. | |
| 6,001,065 A | 12/1999 | De Vito | |
| 6,047,203 A | 4/2000 | Sackner et al. | |
| 6,096,220 A | 8/2000 | Ohkawa | |
| 6,111,466 A | 8/2000 | Mokhtar et al. | |
| 6,134,424 A | 10/2000 | Nishihori et al. | |
| 6,242,911 B1 | 6/2001 | Maschek | |
| 6,254,536 B1 | 7/2001 | De Vito | |
| 6,262,631 B1 | 7/2001 | Li | |
| 6,272,365 B1 | 8/2001 | Ronkainen et al. | |
| 6,289,238 B1 | 9/2001 | Besson et al. | |
| 6,381,482 B1 | 4/2002 | Jayaraman et al. | |
| 6,411,108 B1 | 6/2002 | Douglas et al. | |
| 6,438,413 B1 | 8/2002 | Taheri | |
| 6,472,888 B2 | 10/2002 | Oguma et al. | |
| 6,516,289 B2 | 2/2003 | David | |
| 6,551,252 B2 | 4/2003 | Sackner et al. | |
| 6,577,893 B1 | 6/2003 | Besson et al. | |
| 6,611,168 B1 | 8/2003 | Denison et al. | |
| 6,686,800 B2 | 2/2004 | Krupka | |
| 6,687,523 B1 | 2/2004 | Jayaramen et al. | |
| 6,755,795 B2 | 6/2004 | Marmaropoulos et al. | |
| 6,778,090 B2 | 8/2004 | Newham | |
| 6,783,498 B2 | 8/2004 | Sackner et al. | |
| 6,807,438 B1 | 10/2004 | Brun Del Re et al. | |
| 6,897,788 B2 | 5/2005 | Khair et al. | |
| 6,973,344 B2 | 12/2005 | Finneran et al. | |
| 2001/0056225 A1 | 12/2001 | De Vito | |
| 2002/0038092 A1 | 3/2002 | Stanaland et al. | |
| 2003/0036691 A1 | 2/2003 | Stanaland et al. | |
| 2003/0045804 A1 | 3/2003 | Brodnick | |
| 2003/0212319 A1 | 11/2003 | Magill | |
| 2003/0214408 A1 | 11/2003 | Grajales et al. | |
| 2003/0220553 A1 | 11/2003 | Axelgaard et al. | |
| 2003/0224685 A1 | 12/2003 | Sharma | |
| 2004/0070446 A1 | 4/2004 | Krupka | |
| 2004/0073104 A1 | 4/2004 | Brun Del Re et al. | |
| 2004/0210165 A1 | 10/2004 | Marmaropoulos et al. | |
| 2004/0254435 A1 | 12/2004 | Mathews et al. | |
| 2005/0010096 A1 | 1/2005 | Blackadar | |
| 2005/0054941 A1 | 3/2005 | Ting et al. | |
| 2005/0101873 A1 | 5/2005 | Misczynski et al. | |
| 2005/0113703 A1 | 5/2005 | Farringdon et al. | |
| 2005/0165323 A1 | 7/2005 | Montgomery et al. | |
| 2005/0192488 A1 | 9/2005 | Bryenton et al. | |
| 2005/0234357 A1 | 10/2005 | Xue et al. | |
| 2005/0240087 A1 | 10/2005 | Keenan et al. | |

FOREIGN PATENT DOCUMENTS

| | | |
|---|---|---|
| CA | 2428250 | 11/2003 |
| EP | 282712 | 9/1988 |
| GB | 2353594 | 2/2001 |
| GB | 2388196 | 11/2003 |
| JP | 04-170936 | 6/1992 |
| JP | 07-194563 | 8/1995 |
| WO | WO 93/02616 | 2/1993 |
| WO | 01/16607 | 3/2001 |
| WO | WO 02/071935 | 9/2002 |
| WO | WO 02/093312 | 11/2002 |
| WO | WO 03/034890 | 5/2003 |
| WO | 03/048789 | 6/2003 |
| WO | 03/079897 | 10/2003 |
| WO | WO 2005/032368 | 4/2005 |

OTHER PUBLICATIONS

Clippingdale et al., "Ultra-High Impedance Voltage Probes and Non-Contact Electrocardiography," Sensors: Technology, Systems and Applications, 1st Edition, IOP Publ. Ltd., pp. 469-472, 1991.

Clippingdale et al., "Non-Invasive Dielectric Measurements with the Scanning Potential Microscope," J. Phys. D: Appl. Phys. vol. 27, IOP Publ. Ltd., pp. 2426-2430, 1994.

Clippingdale et al., "Ultrahigh Impedance Capacitively Coupled Heart Imaging Array," Rev. Sci. Instrum., vol. 65, No. 1, pp. 269-270, Jan. 1994.

David et al., "Insulated Electrocardiogram Electrodes," Med. & Biol. Eng., Peter Peregrunis Ltd., vol. 10, pp. 742-751, 1972.

Geddes, L. A., "Electrodes and the Measurement of Bioelectric Events," Wiley-Interscience, pp. 97-106, 1972.

Harland et al., "Electrical Potential Probes—New Directions in the Remote Sensing of the Human Body," Meas. Sci. and Technol., IOP Publ. Ltd., vol. 13, pp. 163-169, 2002.

Harland et al., "Remote Detection of Human Electroencephalograms Using Ultrahigh Input Impedance Electric Potential Sensors," Applied Physics Letters, vol. 81, No. 17, pp. 3284-3286, Oct. 2002.

Harland et al., "High Resolution Ambulatory Electrocardiographic Monitoring Using Wrist-Mounted Electric Potential Sensors," Meas. Sci. and Technol., IOP Publ. Ltd., vol. 14, pp. 923-928, 2003.

Horowitz et al. "The Art of Electronics," 2nd Edition, pp. 96-98, 183-187, 193-207, 209-210, 1989.

Nunez, P. L., "Electric Fields of the Brain: The Neurophysics of EEG," Oxford University Press, New York, pp. 197-198, 1981.

Nunez, P.L. et al., "Spatial-Temporal Structures of Human Alpha Rhythms: Theory, Microcurrent Sources, Multiscale Measurements, and Global Binding of Local Networks," Human Brain Mapping, Wiley-Liss, Inc., vol. 13, pp. 125-164, 2001.

Prance et al., "Electrometer Arrays: Sensing of Spatio-Temporal ELF Fields," Proc. Marelec, London, 3.4, 1997.

Prance et al., "Non-Contact VLSI Imaging Using a Scanning Electric Potential Microscope," Meas. and Sci. Technol., UK, vol. 11, pp. 1229-1235, 1998.

Prance et al., "An Ultra-Low-Noise Electrical-Potential Probe for Human-Body Scanning," Meas. Sci. and Techol., IOP Publ. Ltd., vol. 11, pp. 1-7, 2000.

Richardson, P.C., "The Insulated Electrode: A Pasteless Electrocardiographic Technique," 20th Annual Conference on Engineering in Medicine and Biology, p. 15.7, 1967.

Srebo, R., "Localization of Visually Evoked Cortical Activity in Humans," J. Physiology, Great Britain, vol. 360, pp. 233-246, 1985.

Srinivisan et al., "Spatial Sampling and Filtering of EEG with Spline Laplacians to Estimate Cortical Potentials," Brain Topography, Human Sciences Press, Inc., vol. 8, No. 4, pp. 355-366, 1996.

Foster-Miller Web-Site, http://www.foster-miller.com/t_bt_physiolocial_monitoring.htm.

NewScientist.com Web-Site, http://www.newscientist.com/article.ns?id=dn4255&print=true.

Polar USA Web-Site, http://www.polarusa.com/manufacturers/products/products.asp.

* cited by examiner

UNOBTRUSIVE MEASUREMENT SYSTEM FOR BIOELECTRIC SIGNALS

CROSS-REFERENCE TO RELATED APPLICATIONS

The present invention claims the benefit of the filing dates of U.S. Provisional Patent Application Ser. No. 60/588,045 filed Jul. 15, 2004 entitled UNOBTRUSIVE MEASUREMENT SYSTEM FOR BIOELECTRIC SIGNALS.

BACKGROUND OF THE INVENTION

1. Field of the Invention

The present invention pertains to the art of measuring bioelectric signals and, more particularly, to a system for unobtrusively measuring bioelectric signals developed by an individual.

2. Discussion of the Prior Art

It is widely known that electric fields are developed in free space from many different sources. For example, organs in the human body, including the heart and brain, produce electric fields. For a variety of reasons, it is often desirable to measure these electric fields, such as in performing an electrocardiogram (ECG). Actually, the measuring of bioelectric signals can provide critical information about the physiological status and health of an individual, and are widely used in monitoring, evaluating, diagnosing and caring for patients. Basically, prior methods of measuring electric potentials associated with a human employ securing gel-coated electrodes directly to the skin of a patient. Obviously, this requires preparation and application time, while being quite discomforting to the patient.

More specifically, resistive electrodes have been predominantly employed in connection with measuring electric potentials produced by animals and human beings. As the resistive electrodes must directly touch the skin, preparation of the skin to achieve an adequate resistive connection is required. Such resistive electrodes are the standard for current medical diagnostics and monitoring, but the need for skin preparation and contact rule out expanding their uses. Although attempts have been made to construct new types of resistive electrodes, such as making an electrically conductive fabric, providing a miniature grid of micro-needles that penetrate the skin, and developing chest belt configurations for heart related measurements or elasticized nets with resistive sensors making contact via a conductive fluid for head related measurements, these alternative forms do not overcome the fundamental limitation of needing to directly contact the skin. This limitation leads to an additional concern regarding the inability to maintain the necessary electrical contact based on differing physical attributes of the patient, e.g. amount of surface hair, skin properties, etc.

Another type of sensor that can be used in measuring biopotentials is a capacitive sensor. Early capacitive sensors required a high mutual capacitance to the body, thereby requiring the sensor to also touch the skin of the patient. The electrodes associated with these types of sensors are strongly affected by lift-off from the skin, particularly since the capacitive sensors were not used with conducting gels. As a result, capacitive sensors have not been found to provide any meaningful benefits and were not generally adopted over resistive sensors. However, advances in electronic amplifiers and new circuit techniques have made possible a new class of capacitive sensor that can measure electrical potentials when coupling to a source in the order of 1 pF or less. This capability makes possible the measurement of bioelectric signals with electrodes that do not need a high capacitance to the subject, thereby enabling the electrodes to be used without being in intimate contact with the subject.

To enhance the measurement of bioelectric signals, there still exists a need for a system which can unobtrusively measure the signals with minimal set-up or preparation time. In addition, there exists a need for a bioelectric signal measuring system which is convenient to use, both for the patient and an operator, such as a nurse, doctor or technician. Furthermore, there exists a need for an effective bioelectric signal measuring system which can be used on a patient without the patient being cognitive of the system so as to require an absolute minimum intervention or assistance by the patient, particularly in situations wherein the patient cannot aid a nurse, doctor or the like, such as in the case of an infant or an unconscious individual. Specifically, a truly unobtrusive measurement system which does not require patient preparation is needed.

SUMMARY OF THE INVENTION

The present invention is directed to a system for unobtrusively measuring bioelectric signals developed by an individual, inclusive of a human or animal. The measurement system enables bioelectric signals to be collected through multiple sensors, one or more of which constitutes a capacitive-type sensor, carried by an object against which the individual is positioned. In this manner, the object serves as mounting structure that holds the sensors in place relative to both each other and the individual to assure proper system operation. The sensors are preferably not in direct contact with the skin of the user, but rather are spaced from the user by a layer of material, such as a biocompatible and non-conductive material, e.g. cushioning foam or the like.

In accordance with one embodiment of the invention, the sensor system is formed or otherwise integrated into a pad that can be laid over a chair, stretcher, gurney or bed. In the alternative, the sensor system could be embedded directly in a backrest of the chair, beneath a layer of the stretcher or gurney, or in the foam or fabric associated with the bed. With this arrangement, an individual need only sit in the chair or simply lay on any one of the stretcher, gurney or bed in order for the desired electric signals to be sensed.

Regardless of the particular implementation, the sensor system of the invention is integrated into an object against which an individual rests in a normal manner such as he/she would do when usually encountering the object, to enable bioelectric signals to be continuously measured in an extremely convenient, unobtrusive and effective way, with little or no intervention needed on the part of the individual. Additional objects, features and advantages of the present invention will become more readily apparent from the following detailed description of preferred embodiments when taken in conjunction with the drawings wherein like reference numerals refer to corresponding parts in the several views.

DETAILED DESCRIPTION OF THE PREFERRED EMBODIMENTS

Figure 1:
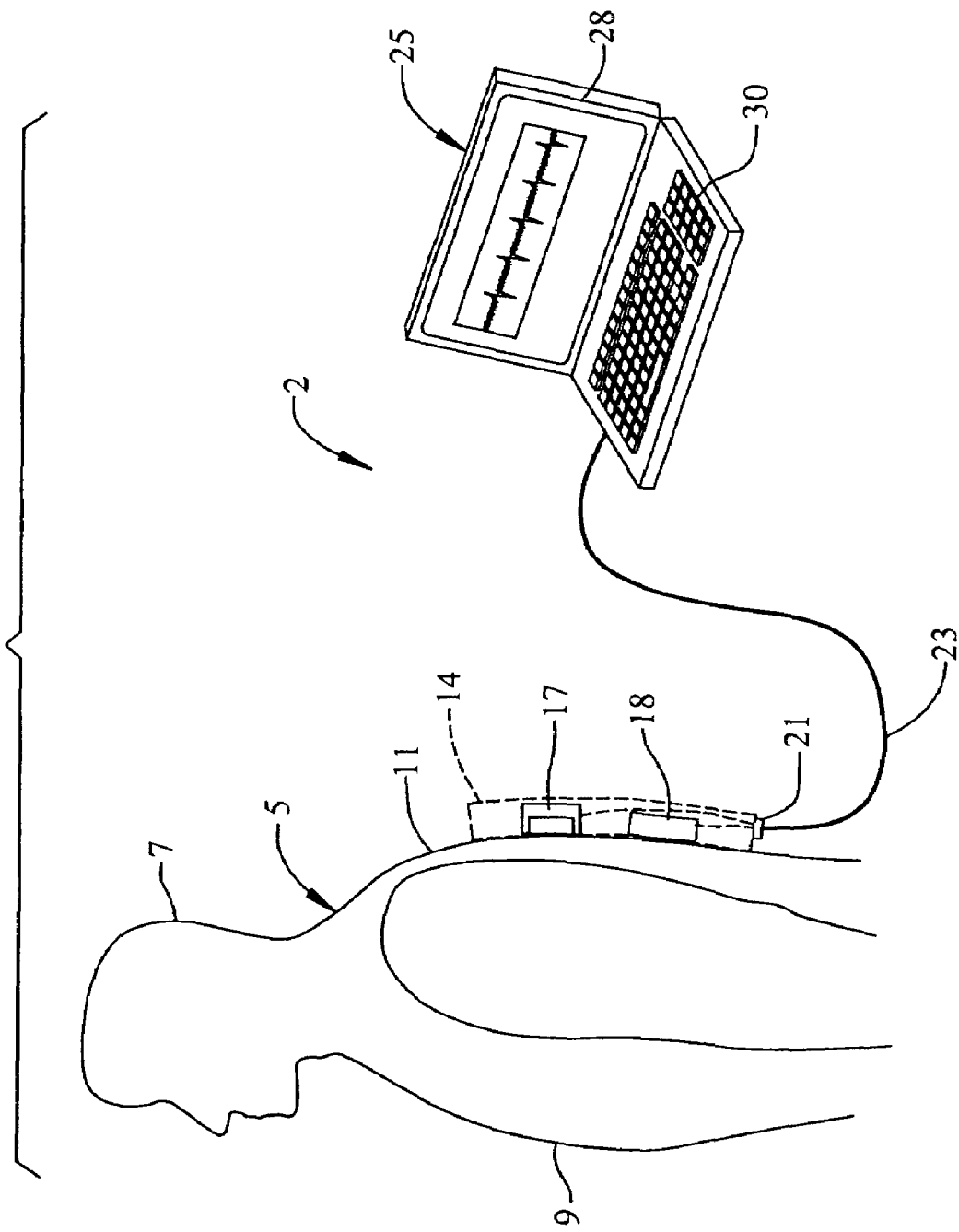
FIG. 1 schematically illustrates the basic sensor system arrangement of the invention.

With initial reference to FIG. 1, a sensor system constructed in accordance with the present invention is generally indicated at 2. In general, sensor system 2 functions to measure biopotentials of an individual 5, such as a medical patient, animal, test subject or the like. As shown, individual 5 includes a head 7, a chest 9 and back 11, with back 11 being positioned against an object which forms part of sensor system 2. In the embodiment shown, the object constitutes a pad 14. More specifically, sensor system 2 includes pad 14 having embedded or otherwise integrated therein at least first and second sensors 17 and 18. In accordance with the invention, at least first sensor 17 constitutes a capacitive-type sensor and, in the most preferred embodiment of the invention, both first and second sensors 17 and 18 constitute capacitive-type sensors.

As shown, each of first and second sensors 17 and 18 is preferably hardwired to a connector 21 and linked through a cable 23 to a remote control unit 25 of sensor system 2. In the embodiment shown, control unit 25 constitutes a laptop computer having a display panel 28 and a keyboard 30. As will be detailed more fully below, the use of sensor system 2 enables individual 5 to be supported against pad 14 whereby a bioelectric field produced by individual 5 can be sensed through first and second sensors 17 and 18, with bioelectric signals being transmitted to control unit 25 for analysis and display purposes. That is, individual 5 will inherently produce time-varying potentials which will be sensed through first and second sensors 17 and 18. As first and second sensors 17 and 18 preferably constitute capacitive-type sensors, no electrically conducting path to individual 5 is needed. In other words, no flow of real current (electrons) occur between individual 5 and first and second sensors 17 and 18 such that first and second sensors 17 and 18 need not be in physical contact with individual 5. Therefore, the use of capacitive-type sensors enables first and second sensors to be embedded or otherwise integrated into an object against which individual 5 is positioned. Various particular embodiments of the invention will be set forth below but, at this point, it should simply be noted that sensor system 2 can be employed to measure the bioelectric field associated with individual 5 by simply supporting individual 5 against pad 14. In this manner, an extremely unobtrusive and convenient sensing system is established which requires no specific set-up or intervention.

Figure 2:
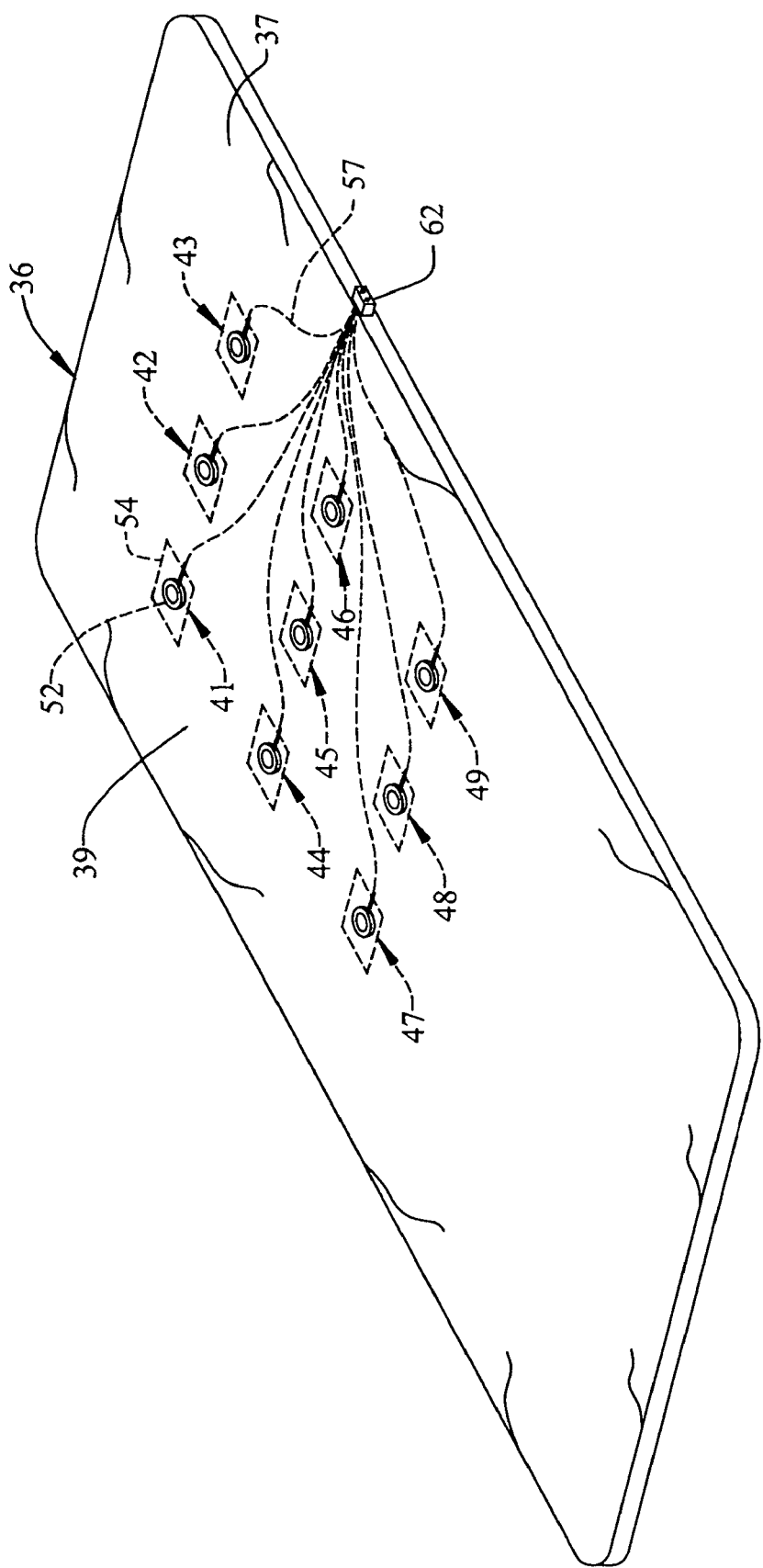
FIG. 2 is a perspective view illustrating the incorporation system of the invention directly into a mat or pad.

Reference will now be made to FIG. 2 which depicts a particular embodiment of the invention. In accordance with this embodiment, sensor system 2 is incorporated into a pad or mat 36 including a cushion layer 37 which is preferably constituted by foam or another biocompatible and non-conductive material. Embedded within pad 36 is a sensor array 39 which is shown to include a plurality of sensors 41–49. As shown, sensors 41–49 are arranged in various row and columns. However, sensors 41–49 can actually be more randomly arranged or repositionable relative to pad 36. In any case, each sensor 41–49 preferably constitutes a capacitive-type sensor and includes a capacitive-type electrode 52 having an associated mounting strip 54. Each electrode 52 is linked through one or more conductors 57 to a connector 62 that is exposed from pad 36. Connector 62 is adapted to be interconnected to a control unit 25.

Figure 3:
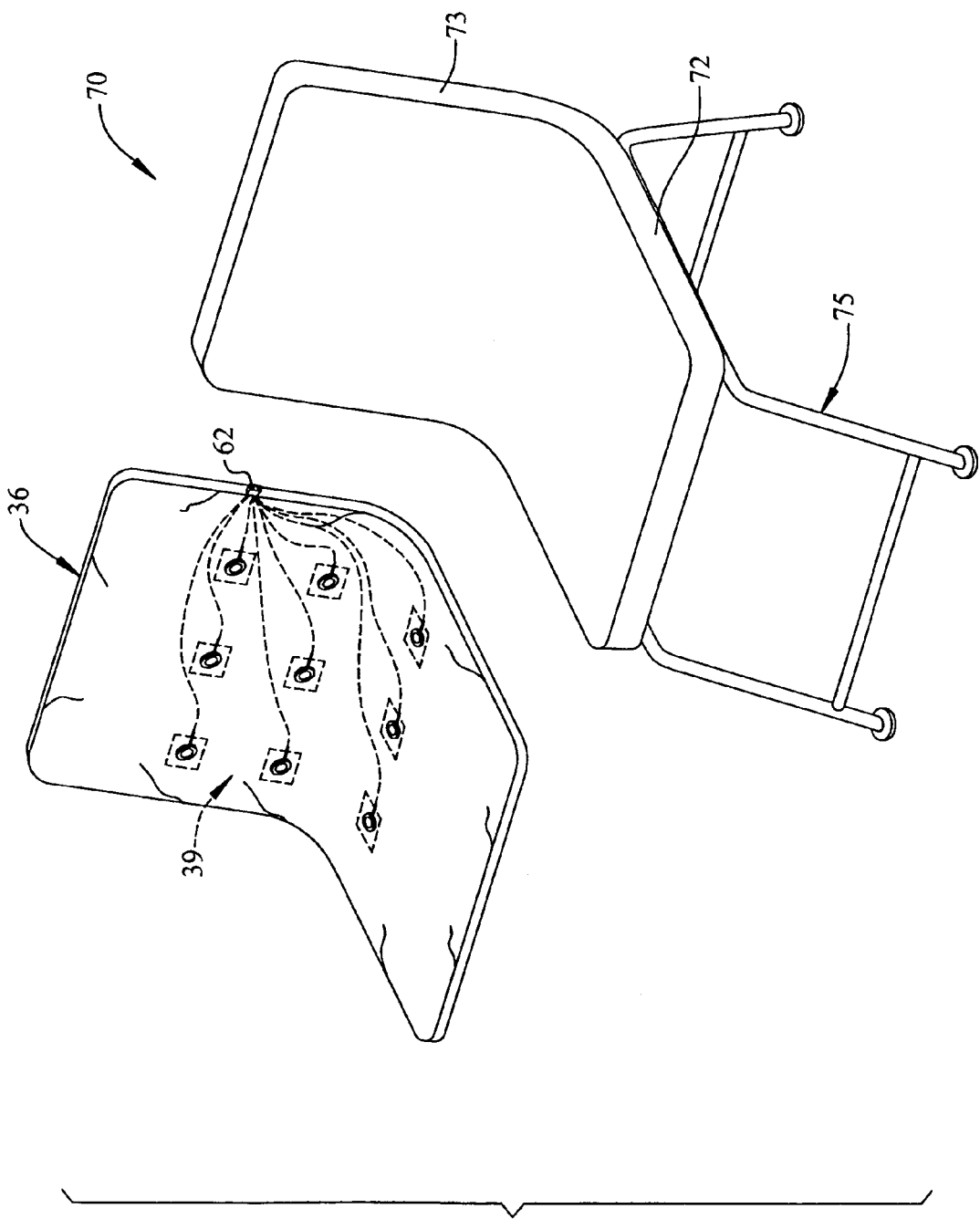
FIG. 3 is a perspective view illustrating the use of the sensor system of the invention in combination with a chair.

Pad 36 can take various shapes and forms in accordance with the invention, including that of pad 14. FIG. 3 illustrates an arrangement wherein pad 14 conforms to, and is adapted to be supported upon, a chair 70. As shown, chair 70 includes a seat portion 72, a back portion 73 and a supporting frame 75. Once pad 36 is laid upon both seat portion 72 and back portion 73 and interconnected to control unit 25, individual 5 need only sit in chair 70 in order for sensor system 2 to be able to sense the bioelectric field developed by individual 5. As individual 5 does not need to be prepped, such as by having electrodes directly attached to back 11, individual 5 is not at all inconvenienced and, in fact, may not even be aware that the bioelectric field is being sensed. Through the use of capacitive-type sensors 41–49, the bioelectric signals can even be advantageously sensed through clothing worn by individual 5, as well as cushion 37 of pad 36.

Figure 4:
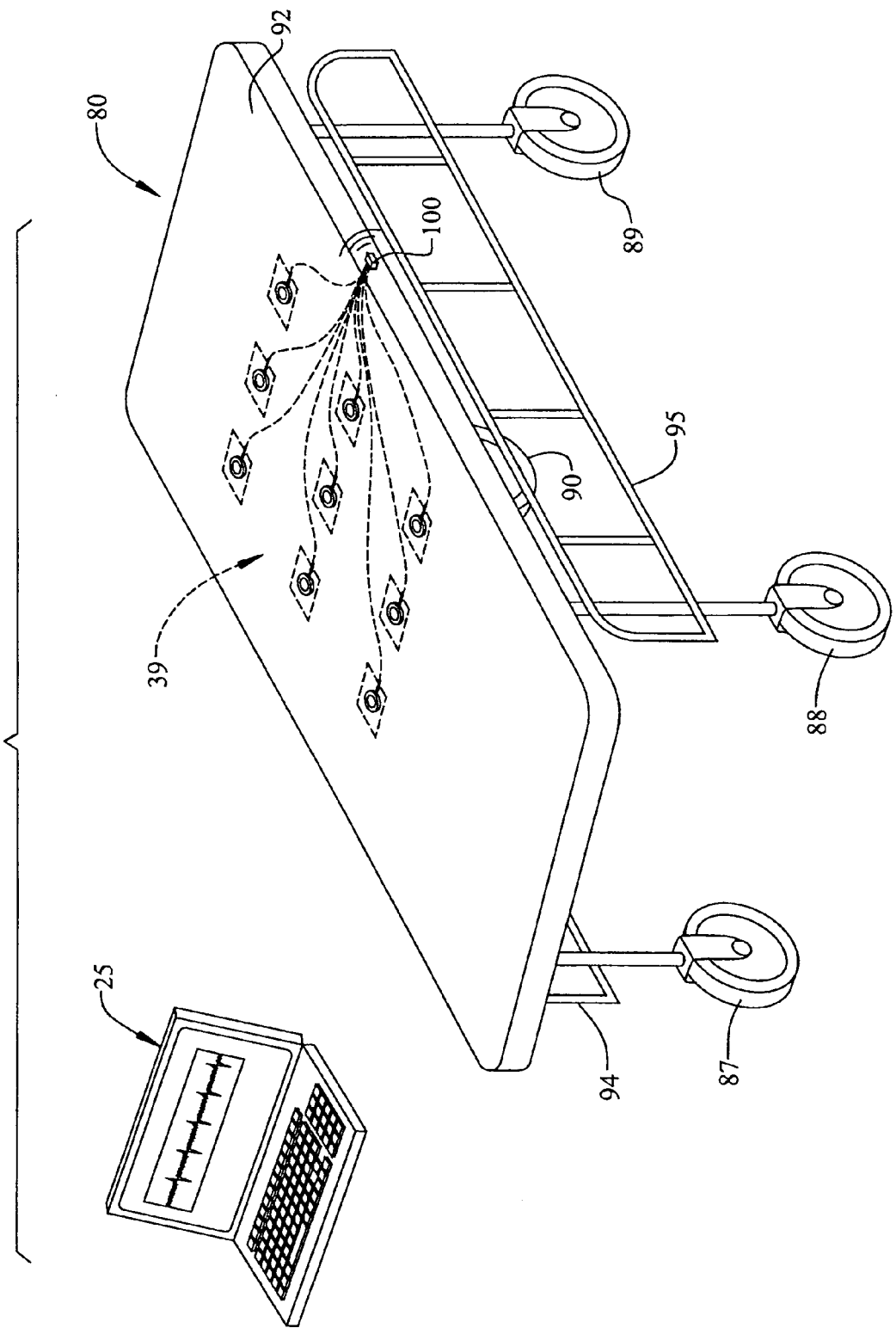
FIG. 4 is a perspective view illustrating the use of the sensor system of the invention in combination with a stretcher or gurney.

Based on the above, it should be readily apparent that sensor system 2 of the present invention can be incorporated into various objects against which an individual 5, who produces a bioelectric field to be measured, is adapted to be supported. Although sensor array 39 is shown in FIG. 3 to be incorporated into pad 36 that is placed upon chair 70, it should be realized that other arrangements are possible in accordance with the invention, such as having sensor array 39 directly integrated into seat and/or back portions 72 and 73 of chair 70. FIG. 4 illustrates another embodiment of the invention wherein sensor system 2 is incorporated into a stretcher or gurney 80 which is supported by casters 87–90 for mobility purposes. In any case, gurney 80 includes a table portion 92, as well as side protectors or rails 94 and 95. As shown, sensor array 39 is embedded within table portion 92. With this arrangement, individual 5 need merely lay, either on chest 9 or back 11, on table portion 92 in order for measuring of the bioelectric field.

Figure 5:
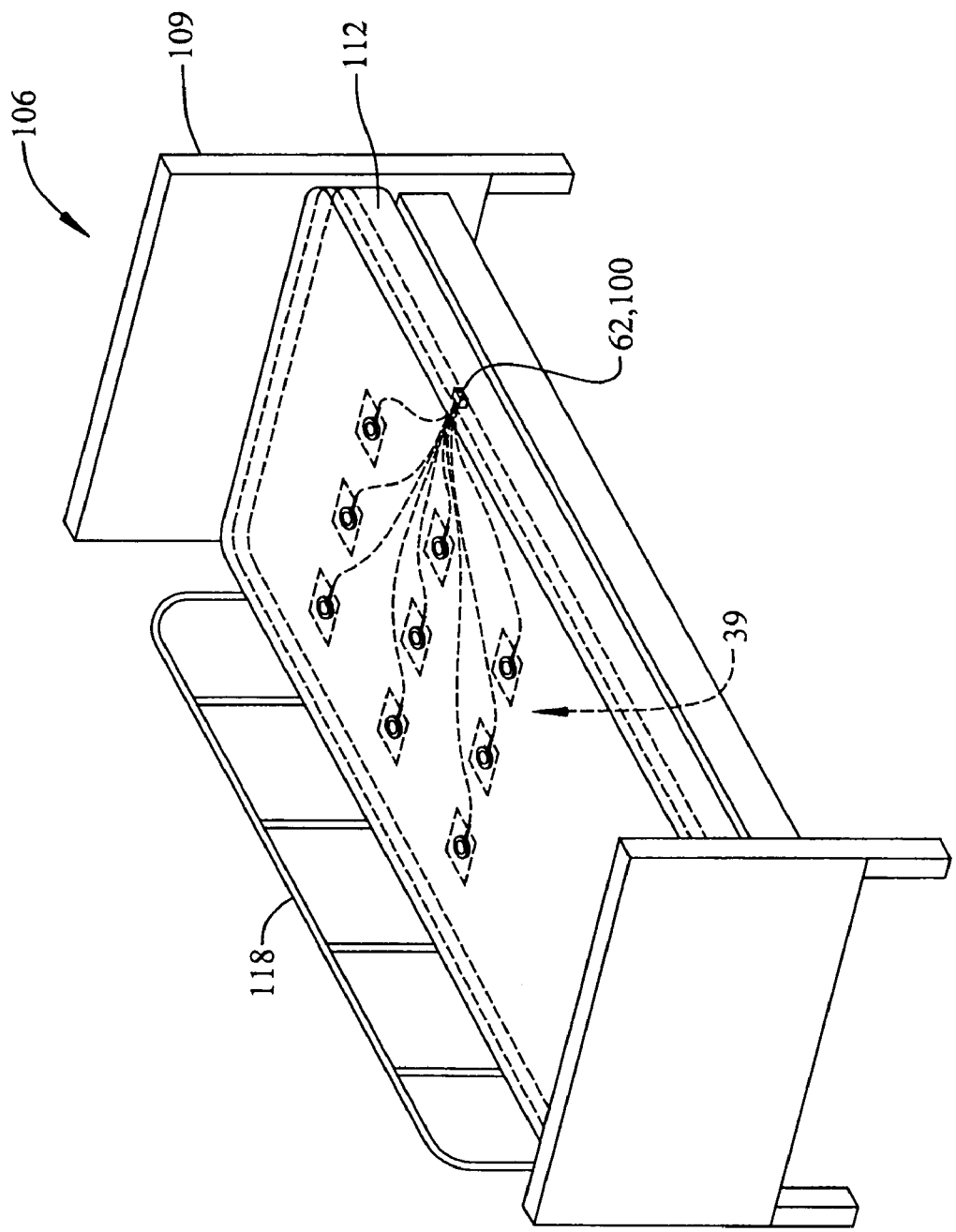
FIG. 5 is a perspective view illustrating the use of the sensor system of the invention in combination with a bed.

FIG. 4 also illustrates another aspect of the present invention. In the embodiment set forth above, sensor array 39 was linked to control unit 25 through a cable 23. In this embodiment, the plurality of sensors 41–49 are linked through a connector 100 which constitutes a wireless transmitter. With this arrangement, RF, infrared or the like type signals can be employed to communicate sensor array 39 to control unit 25. FIG. 5 illustrates a still further embodiment of the invention wherein sensor system 2 is incorporated into a bed 106 having a frame 109 and a mattress 112. More specifically, sensor array 39 is embedded into mattress 112 or other cushion which has exposed therefrom an associated connector 21, 100.

As indicated above, sensor system 2 of the present invention constitutes an unobtrusive measurement system for bioelectric fields. To this end, sensor array 39 is naturally brought into adequate physical proximity to individual 5 by merely positioning a respective body portion of individual 5 against the object, whether it be pad 14, pad 36, chair 70, gurney 80, bed 106, a crib, an incubator, a couch, a wall or the like. To this point, sensor system 2 has been disclosed for use in sensing electric fields produced by a heart of individual 5. However, sensor system 2 of the invention can be employed to measure electric fields produced by other organs of individual 5, such as the brain. In this case, head 7 of individual 5 would be positioned against and supported by an object, such as a cushioned headrest, provided as part of a scanning device into which sensor array 39 is integrated. In any case, sensor system 2 does not require attention from individual 5 for proper operation. For instance, individual 5 need not grip a particular grounding element, apply conducting fluids or the like in order for the electric field to be measured. The object itself serves as the mounting structure that holds the plurality of sensors 41–49 in place relative to individual 5 and to each other. Again, capacitive-type sensors are preferably employed to avoid the need for direct contact with the skin of individual 5 by electrodes 52. In general, capacitive-type sensors 41–49 are able to measure biopotentials with total input capacitance less than approximately 50 pF and preferably less than 1 pF. For each of the chair, gurney and bed embodiments, it is preferred to stack or run averages of multiple sensed wave forms in order to provide a clinical quality electrocardiogram (ECG). Although sensor array 39 is preferably utilized, it is only necessary that two or more sensors be located in the region where the biopotential signal is to be measured. Sensor array 39 is preferably employed in order to enable a select set of sensors 41–49 to be utilized for any given measurement. More specifically, a nurse, doctor, technician or the like can activate select ones of sensors 41–49 through control unit 25 for any given procedure, or a software algorithm can be used to automatically make the selection based on established criteria.

Although described with reference to preferred embodiments of the invention, it should be readily understood that various changes and/or modifications can be made to the invention without departing from the spirit thereof. Regardless of the particular implementation, the sensor system of the invention is integrated into an object against which an individual rests to enable bioelectric signals to be continuously measured in an extremely convenient, unobtrusive and effective manner, with little or no intervention needed on the part of the individual producing the bioelectric field being measured. In the overall system, the bioelectric signals can be pre-processed, either prior to or by the remote control unit. For instance, the difference between the outputs of one or more sensors can be taken before transmitting the data or simply prior to further analyzing the data. In any event, the invention is only intended to be limited by the scope of the following claims.

We claim:

1. A sensor system for measuring biopotentials of an individual comprising:
   an object against which an individual, who produces a bioelectric field to be measured, is adapted to be supported; and
   a plurality of electrical sensors integrated into the object, at least one of the plurality of electrical sensors being constituted by a capacitive-type electrical sensor having an associated layer of biocompatible non-conductive material preventing the conduction of direct current, wherein the bioelectric field with a total input capacitance of less than approximately 50 pF can be unobtrusively measured.

2. The sensor system according to claim 1, wherein the plurality of electrical sensors are embedded into the object.

3. The sensor system according to claim 1, further comprising: a power source for the plurality of electrical sensors, said power source being carried by the object.

4. The sensor system according to claim 3, wherein the power source constitutes a battery.

5. The sensor system according to claim 1, further comprising: means for transferring bioelectric signals from the plurality of electrical sensors to a position remote from the object.

6. The sensor system according to claim 5, wherein the transferring means includes at least one connector which is at least partially exposed from the object.

7. The sensor system according to claim 5, further comprising: means for receiving bioelectric signals measured from the plurality of electrical sensors, said receiving means being linked to the transferring means.

8. The sensor system according to claim 7, wherein said receiving means further processes, stores and displays the bioelectric signals.

9. The sensor system according to claim 5, wherein said transferring means constitutes a wireless communication link.

10. The sensor system according to claim 1, wherein the object constitutes a pad, with said plurality of electrical sensors being embedded in the pad.

11. The sensor system according to claim 1, wherein the plurality of electrical sensors are arranged in an array about the object.

12. The sensor system according to claim 11, further comprising: means for choosing select ones of the plurality of electrical sensors in the array to sense the bioelectric field.

13. The sensor system according to claim 1, wherein the object constitutes a chair.

14. The sensor system according to claim 1, wherein the object constitutes a bed.

15. The sensor system according to claim 14, wherein the bed includes a mattress, said plurality of electrical sensors being embedded in the mattress.

16. A method of sensing bioelectric signals from an individual producing a bioelectric field comprising:
   supporting a body portion of the individual against an object having a plurality of electrical sensors integrated therein, with at least one of the plurality of electrical sensors being constituted by a capacitive-type sensor;
   preventing conduction of direct current between the individual and the capacitive-type sensor by placing an associated layer of biocompatible non-conductive material between the individual and the capacitive-type sensor;
   measuring bioelectric signals, including bioelectric signals with a total input capacitance of less than approximately 50 pF, with the plurality of electrical sensors; and
   transmitting the bioelectric signals associated with the bioelectric field to a remote location for analysis.

17. The method of claim 16, wherein supporting the body portion against the object constitutes laying the individual down on the object.

18. The method of claim 16, wherein supporting the body portion against the object constitutes sitting the individual in a chair.

19. The method of claim 16, further comprising: selecting ones of the plurality of electrical sensors from an array of the plurality of electrical sensors which are embedded into the object.

20. The method of claim 16, further comprising: employing a wireless communication link in transmitting the bioelectric signals.

* * * * *